US006767993B2

(12) United States Patent
Bray et al.

(10) Patent No.: US 6,767,993 B2
(45) Date of Patent: Jul. 27, 2004

(54) METHODS AND COMPOSITIONS FOR PEPTIDE SYNTHESIS

(76) Inventors: Brian Bray, 1912 Broadway Dr., Graham, NC (US) 27253; Marc Andersen, 4108 Balsam Dr., Raleigh, NC (US) 27612; Paul Erickson Friedrich, 4208 Wyckford Pl., Apex, NC (US) 27502; Myung-Chol Kang, 193 Landing Dr., Chapel Hill, NC (US) 27514

( * ) Notice: Subject to any disclaimer, the term of this patent is extended or adjusted under 35 U.S.C. 154(b) by 223 days.

(21) Appl. No.: 10/109,748

(22) Filed: Mar. 29, 2002

(65) Prior Publication Data

US 2003/0125516 A1 Jul. 3, 2003

Related U.S. Application Data

(62) Division of application No. 09/349,205, filed on Jul. 7, 1999, now Pat. No. 6,469,136.

(51) Int. Cl.$^7$ .......................... C12P 21/06; A61K 38/00; C07K 16/00; C07K 1/00; A23J 1/00
(52) U.S. Cl. ...................... 530/333; 435/69.1; 530/300; 530/333; 530/350; 530/402; 530/412
(58) Field of Search .......................... 435/69.1; 530/300, 530/333, 350, 402, 412

(56) References Cited

U.S. PATENT DOCUMENTS

| 5,358,934 A | 10/1994 | Borovsky et al. |
| 5,464,933 A | 11/1995 | Bolognesi et al. |
| 5,656,480 A | 8/1997 | Wild et al. |

FOREIGN PATENT DOCUMENTS

| WO | WO 94/28920 | 12/1994 |
| WO | WO 94/28929 | 12/1994 |
| WO | WO 96/19495 | 6/1996 |
| WO | WO 00/12233 | 5/1999 |
| WO | WO 99/48513 | 9/1999 |
| WO | WO 99/59615 | 11/1999 |

OTHER PUBLICATIONS

Barlos et al., 1989, "The Synthesis of Protected Peptide Fragments Using Substituted Triphenylmethyl Resins", Tetrahedron Lett. 30:3943–3946.
Carpino and Han, 1972, "The 9–Fluorenylmethoxycarbonyl Amino–Protecting Group", J. Org. Chem. 37:3404–3409.
Carpino and Han, 1972, "The 9–Fluorenylmethoxycarbonyl Function, a New Base–Sensitive Amino–Protecting Group", J. Am. Chem. Soc. 92:5748–5749.
Creighton, 1983, *Proteins: Structures and Molecular Principles*, W.H. Freeman and Co., New York, table of contents.
Kamber and Riniker, 1992, "The Solid Phase Synthesis of Protected Peptides Combined With Fragment Coupling in Solution", in: *Peptides, Chemistry and Biology*, (Proc. 12$^{th}$ American Peptide Symposium, Jun. 16–21, 1991, Cambridge, MA), Smith and Rivier, eds., ESCOM Science Publishers, pp. 525–526.
Mergler et al., 1988, "Peptide Synthesis by a Combination of Solid–Phase and Solution Methods I: A New Very Acid Labile Anchor Group for the Solid Phase Synthesis of Fully Protected Fragments", Tetrahedron Lett. 29:4005–4008.
Mergler et al., 1988, "Peptide Synthesis by a Combination of Solid–Phase and Solution Methods II: Synthesis of Fully Protected Peptide Fragments on 2–Methoxy–4–Alkoxy–Benzyl Alcohol Resin" Tetrahedron Lett. 29:4009–4012.
Richter and Gadek, 1994, "A Surprising Observation about Mistsunobu Reactions in Solid Phase Synthesis", Tetrahedron Lett. 35:4705–4706.
Riniker et al., 1993, "A General Strategy for the Synthesis of Large Peptides: The Combined Solid–Phase and Solution Approach", Tetrahedron Lett. 49:9307–9320.
Sieber, 1987, "An Improved Method for Anchoring of 9–Fluorenylmethoxycarbonyl–Amino Acids to 4–Alkoxybenzyl Alcohol Resins", Tetrahedron Lett. 28:6147–6150.
Sole and Barnay, 1992, "Optimization of Solid–Phase Synthesis of [Ala$^8$]–dynorphin A $^{1-3}$", J. Org. Chem. 57–5399–5403.
Lawless et al. HIV–1 membrane fusion mechanism: structural studies of the interactions between biologically–active peptides from gp41. Biochemistry. Oct. 22, 1996;35(42):13697–13708.
Wild et al. Peptides corresponding to a predictive alpha–helical domain of human immunodeficiency virus type 1 gp41 are potent inhibitors of virus infection. Proc Natl Acad Sci U S A. Oct. 11, 1994;91(21):9770–9774.

*Primary Examiner*—Kenneth R. Horlick
*Assistant Examiner*—Young J. Kim

(57) ABSTRACT

The present invention relates, first, to methods for the synthesis of peptides referred to as T-1249 and T-1249-like peptides. Such methods utilize solid and liquid phase synthesis procedures to synthesize and combine groups of specific peptide fragments to yield the peptide of interest. The present invention further relates to individual peptide fragments which act as intermediates in the synthesis of the peptides on interest (e.g., T-1249). The present invention still further relates to groups of such peptide intermediate fragments which can be utilized together to produce full-length T-1249 and T-1249-like peptides.

25 Claims, 2 Drawing Sheets

METHODS AND COMPOSITIONS FOR PEPTIDE SYNTHESIS

Figure 1A:
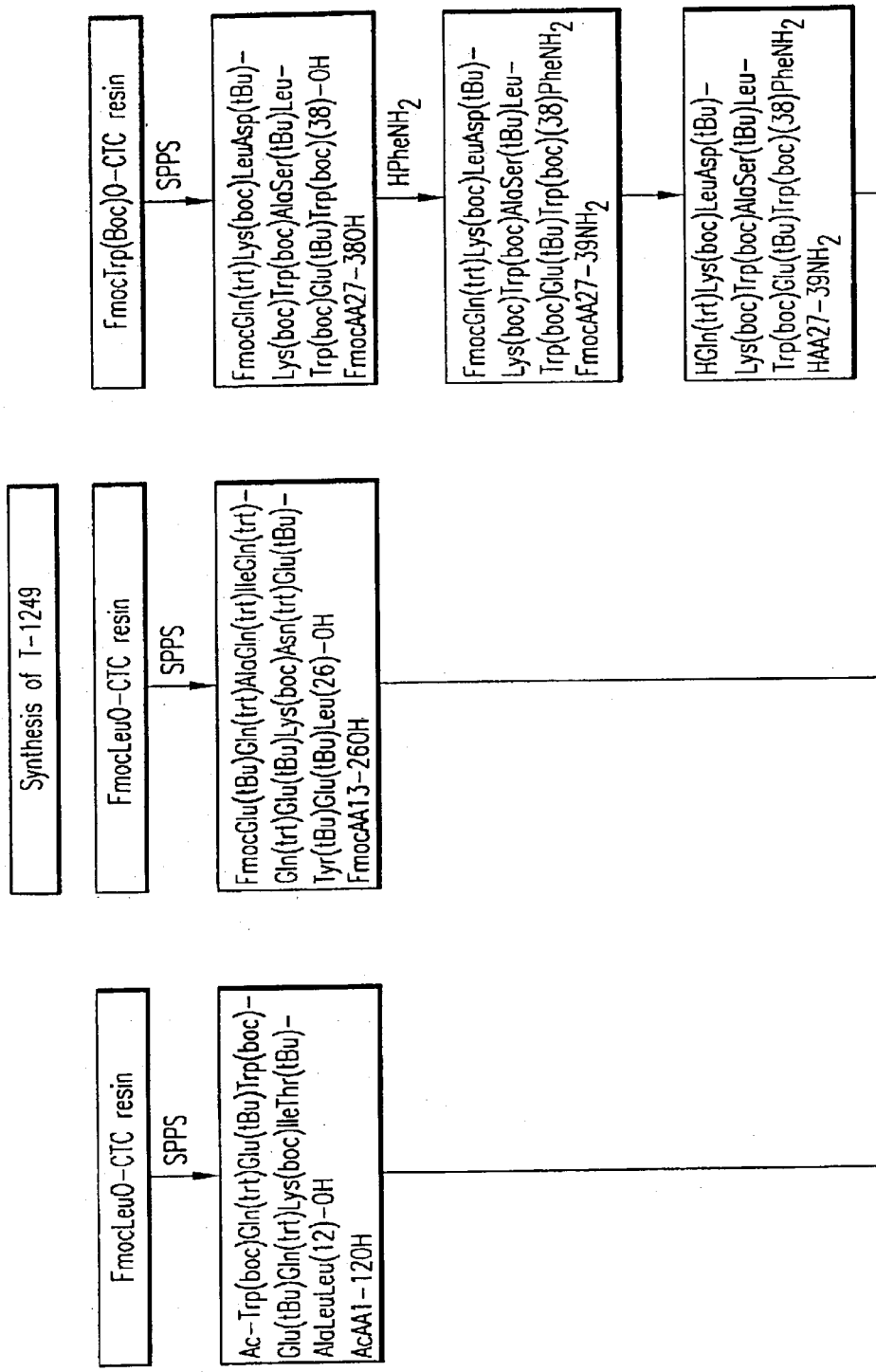

This application is a division of application Ser. No. 09/349,205, filed Jul. 7, 1999, now U.S. Pat. No. 6,469,136, which is incorporated herein by reference in its entirety.

1. INTRODUCTION

The present invention relates, first, to methods for the synthesis of peptides, in particular peptides referred to herein as T-1249 (SEQ ID NO:1) and T-1249-like peptides. Such methods utilize solid and liquid phase synthesis procedures to synthesize and combine groups of specific peptide fragments to yield the peptide of interest. The present invention further relates to individual peptide fragments which can act as intermediates in the synthesis of the peptides of interest (e.g., T-1249). The present invention still further relates to groups of such peptide intermediate fragments which can be utilized together to produce full-length T-1249 and T-1249-like peptides. The present invention still further relates to methods for the purification of peptides, in particular T-1249 and T-1249-like peptides, and the individual peptide fragments which act as intermediates in the synthesis of the subject peptides.

2. BACKGROUND

Recently, a large number of peptides have been identified which exhibit an ability to inhibit fusion-associated events, and, importantly, also exhibit potent antiviral activity. See, for example, U.S. Pat. Nos. 5,464,933; 5,656,480; PCT Publication Nos. WO 94/28920; WO 96/19495. As these peptides come to be used extensively, for example as therapeutics, the need arises for an ability to synthesize them in large scale quantities.

While techniques exist for peptide synthesis, (see, e.g., Mergler et al., 1988, Tetrahedron Letters 29:4005–4008; Mergler et al., 1988, Tetrahedron Letters 29:4009–4012; Kamber et al. (eds), "Peptides, Chemistry and Biology, ESCOM, Leiden, 1992, 525–526; and Riniker et al., 1993, Tetrahedron Letters 49:9307–9320) no techniques currently exist which can be utilized for large scale, economical production of easily purified peptides such as T-1249.

3. SUMMARY OF THE INVENTION

The present invention relates, first, to methods for the synthesis of peptides, in particular peptides referred to herein as T-1249 (SEQ ID NO:1) and T-1249-like peptides. Such methods utilize solid and liquid phase synthesis procedures to synthesize and combine groups of specific peptide fragments to yield the peptide of interest. Generally, the methods of the invention comprise synthesizing specific side-chain protected peptide fragment intermediates of T-1249 or a T-1249-like peptide on a solid support, coupling the protected fragments in solution to form a protected T-1249 or T-1249-like peptide, followed by deprotection of the side chains to yield the final T-1249 or T-1249-like peptide. A preferred embodiment of the methods of the invention involves the synthesis of a T-1249 peptide having an amino acid sequence as depicted in SEQ ID NO:1.

The present invention further relates to individual peptide fragments which act as intermediates in the synthesis of the peptides of interest (e.g., T-1249). The peptide fragments of the invention include, but are not limited to, those having amino acid sequences as depicted in Table 1 below:

TABLE 1

| PEPTIDE NO. | AMINO ACID SEQUENCE | | CORRESPONDING NUMBERED AMINO ACID SEQUENCE OF T-1249 (SEQ. ID NO:1) |
|---|---|---|---|
| 1 | WQEWEQKITALL | (SEQ ID NO:2) | 1–12 |
| 2 | EQAQIQQEKNEYEL | (SEQ ID NO:3) | 13–26 |
| 3 | QKLDKWASLWEW | (SEQ ID NO:4) | 27–38 |
| 4 | QKLDKWASLWEWF | (SEQ ID NO:5) | 27–39 |
| 5 | EQAQIQQEKNEYELQKLDKWASLWEWF | (SEQ ID NO:6) | 13–39 |
| 6 | WQEWEQKITALLEQAQIQQEKNEYEL | (SEQ ID NO:7) | 1–26 |
| 7 | EQAQIQQEKNEYELQKLDKWASLWEW | (SEQ ID NO:8) | 13–38 |

The present invention still further relates to particular groups of peptide fragments which act as intermediates in the synthesis of the peptide of interest. The groups of peptide fragments according to the invention include Groups 1–6, as designated in Table 2 below.

TABLE 2

| Group | Amino Acid Sequence | | Corresponding Numbered Amino Acid Sequence of T-1249 (SEQ. ID NO:1) |
|---|---|---|---|
| 1 | WQEWEQKITALL | (SEQ ID NO:2) | 1–12 |
|   | EQAQIQQEKNEYEL | (SEQ ID NO:3) | 13–26 |
|   | QKLDKWASLWEW | (SEQ ID NO:4) | 27–38 |
| 2 | WQEWEQKITALL | (SEQ ID NO:2) | 1–12 |
|   | EQAQIQQEKNEYEL | (SEQ ID NO:3) | 13–26 |
|   | QKLDKWASLWEWF | (SEQ ID NO:5) | 27–39 |
| 3 | WQEWEQKITALL | (SEQ ID NO:2) | 1–12 |
|   | EQAQIQQEKNEYELQKLDKWASLWEWF | (SEQ ID NO:6) | 13–39 |
| 4 | WQEWEQKITALL | (SEQ ID NO:2) | 1–12 |
|   | EQAQIQQEKNEYELQKLDKWASLWEW | (SEQ ID NO:8) | 13–38 |
| 5 | WQEWEQKITALLEQAQIQQEKNEYEL | (SEQ ID NO:7) | 1–26 |
|   | QKLDKWASLWEW | (SEQ ID NO:4) | 27–38 |
| 6 | WQEWEQKITALLEQAQIQQEKNEYEL | (SEQ ID NO:7) | 1–26 |
|   | QKLDKWASLWEWF | (SEQ ID NO:5) | 27–39 |

This invention is based, in part, on the inventors' unexpected discovery that certain combinations of solid phase liquid phase synthetic reactions allow high purity T-1249 and T-1249-like peptides to be manufactured for the first time on a large scale with high throughput and high yield. In particular, in accordance with the methods of the invention, T-1249 and T-1249-like peptides may be synthesized on a scale of one or more kilograms. It has been found that by selecting the specific T-1249 peptide fragments of the invention for solid phase synthesis, the highly efficient coupling of solid phase techniques may be exploited without having to use the 3-, 4- or even 5-fold excess of amino acids and reagents that are normally required in solid phase synthesis. The methods of the invention use only about an 0.5-fold excess (about 1.5 equivalents) of amino acid in the solid phase synthesis of the peptide fragments of the invention. This reduction in the amount of amino acid and reagents makes the methods of the invention suitable for large scale synthesis of T-1249 and T-1249-like peptides.

In addition, the inventors have surprisingly found that certain peptide fragments may be synthesized in the solid phase at a loading of about >0.5 mmol per gram of solid phase resin. This loading significantly enhances throughput over the loading range of 0.25 to 0.35 mmol per gram of resin typically achieved in solid phase peptide synthesis. Moreover, the inventors have found that synthesizing selected peptide fragments in the solid phase using super acid sensitive resin produces peptide fragments of unusually high purity. Chromatographic techniques are not necessary to purify the peptide fragments produced according to the invention; the fragments are simply put through precipitation and/or trituration steps before use, or used as obtained directly from the resin. Use of a super acid sensitive resin allows the synthesized, protected peptides of the invention to be cleaved from the resin without concomitant removal of the side-chain protecting groups. This reduces impurities, and allows peptides comprising 10 amino acids or greater to be synthesized in high purity and yield.

The impurity profile of T-1249 and T-1249-like peptides which are synthesized in the solution phase according to the methods of the invention by coupling of the high purity peptide fragments produced according to the invention consists of fragments that did not couple, and contains significantly lower levels of closely related deletion analogues than T-1249 and T-1249-like peptides synthesized according to conventional techniques, e.g., solely solid phase synthesis. Accordingly, T-1249 and T-1249-like peptides produced according to the invention are much easier to purify than those produced according to conventional techniques. In particular, T-1249 produced according to the methods of the present invention may be easily purified to >90% purity in single pass chromatography. For example, in accordance with the methods of the invention, T-1249 can be purified in amounts of 400 g or more using a 5 inch column. In contrast, T-1249 prepared using conventional solid phase synthesis (SPPS) is very difficult to purify, requiring multiple pass chromatography. By way of example, purification of T-1249 prepared by SPPS typically results in 10 grams or less of purified material from an 8 inch column.

The Examples presented in Section 9 below, demonstrate such combinatorial syntheses of T-1249 full-length peptides. The T-1249 and T-1249-like peptides and intermediates may be produced on a scale of one or more kilograms by the methods of the invention.

The present inventors have also unexpectedly found that peptides such as T-1249 and other T-1249-like peptides, as well as certain peptide fragments described herein may be purified using high capacity materials because of the high purity of T-1249 after solution phase synthesis. Thus, the present invention still further relates to methods for the purification of peptides, in particular T-1249 and T-1249-like peptides, and the individual peptide fragments which act as intermediates in the synthesis of the subject peptides.

3.1 DEFINITIONS

The amino acid notations used herein are conventional and are as follows:

| Common Amino Acid Abbreviations | | |
|---|---|---|
| Amino Acid | One-Letter Symbol | Common Abbreviation |
| Alanine | A | Ala |
| Asparagine | N | Asn |
| Aspartic acid | D | Asp |
| Glutamine | Q | Gln |
| Glutamic acid | E | Glu |
| Isoleucine | I | Ile |
| Leucine | L | Leu |
| Lysine | K | Lys |
| Phenylalanine | F | Phe |
| Serine | S | Ser |
| Threonine | T | Thr |
| Tryptophan | W | Trp |
| Tyrosine | Y | Tyr |

4. BRIEF DESCRIPTION OF THE FIGURES

Figure 1B:
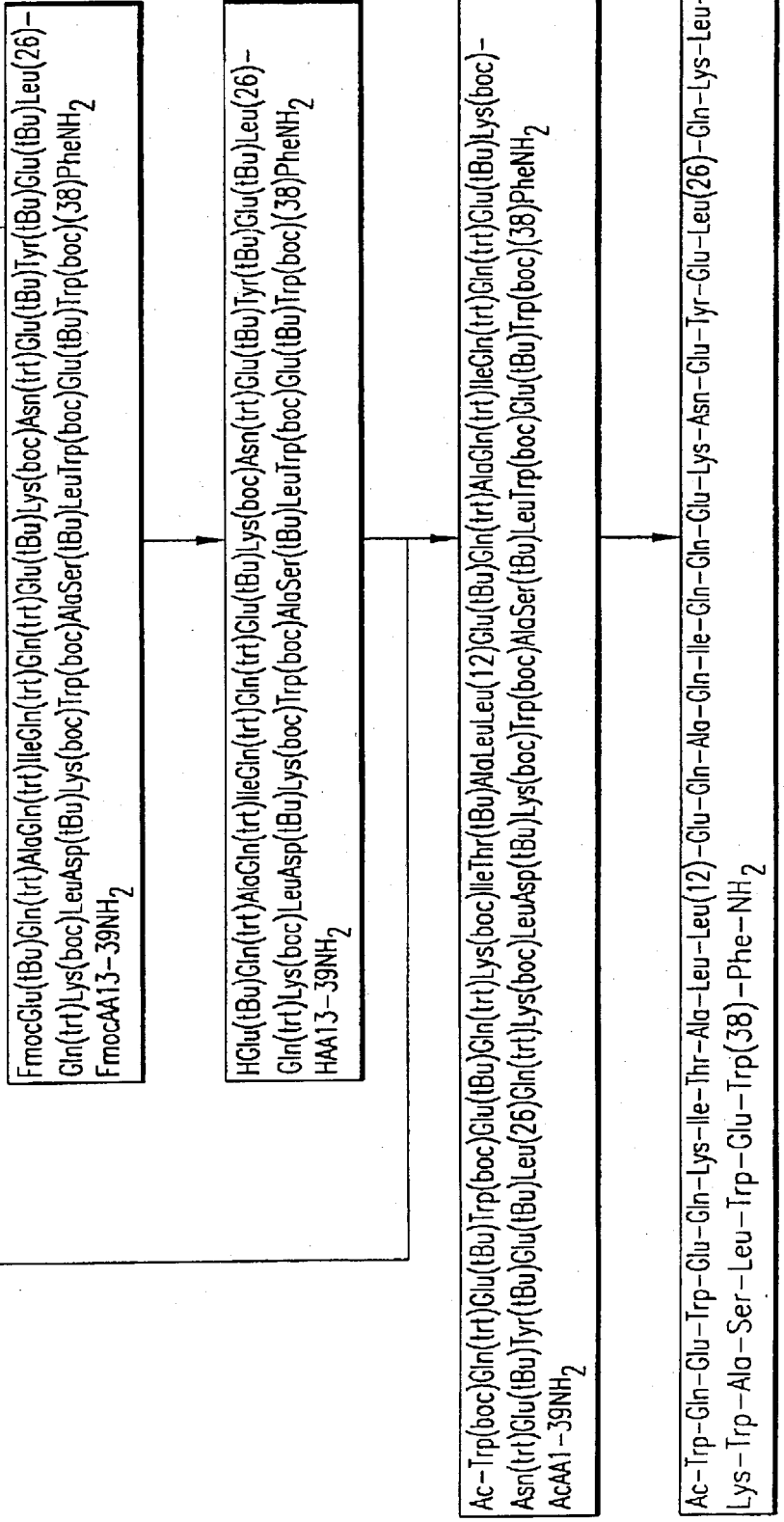

FIG. 1: T-1249 three fragment approach. This figure depicts the scheme followed in the Example presented in Sections 8 and 9 below, for the synthesis of full-length T-1249 beginning with intermediate peptide fragment Group 1, as shown in Table 2, above, and depicts one, non-limiting embodiment of the methods of the invention.

5. DETAILED DESCRIPTION OF THE INVENTION

5.1 FULL-LENGTH PEPTIDES

The present invention relates to methods, peptide fragments, groups of peptide fragments which can be used to synthesize the peptide known as T-1249. T-1249 is a 39 amino acid residue polypeptide whose sequence is derived from HIV-1, HIV-2 and SIV gp41 viral polypeptide sequences. T-1249 has the following amino acid sequence:

$NH_2$-WQEWEQKITALLEQAQIQQEKNEYELQ KLDKWASLWEWF-COOH

It will be understood that the methods, fragments and groups of fragments and techniques utilized for choosing the fragments and groups of fragments of the present invention may be used to synthesize T-1249-like fragments in addition to T-1249. The term "T-1249-like" as used herein means any HIV or non-HIV peptide listed in International Publication No. PCT/US99/11212, filed May 20, 1999, which is hereby incorporated by reference in its entirety.

In addition to T-1249 and the T-1249-like peptides described above, the methods, fragments and groups of fragments of the present invention may be used to synthesize peptides having modified amino and/or carboxyl terminal ends. Taking T-1249 as an example, such peptides can be of the formula:

X-WQEWEQKITALLEQAQIQQEKNEYELQKLDK WASLWEWF-Z wherein X represents an amino group; a hydrophobic group selected from the group consisting of carbobenzoxyl, dansyl, and T-butyloxycarbonyl; an acetyl group; a 9-fluoroenyl-methoxy-carbonyl (FMOC) group; or a macromolecular carrier group selected from the group consisting of lipid-fatty acid conjugates, polyethylene glycol, and carbohydrates; and Z represents a carboxyl group; an amido group; a T-butyloxycarbonyl group; a para-nitrobenzyl ester group; or a macromolecular carrier group selected from the group consisting of lipid-fatty acid conjugates, polyethylene glycol, and carbohydrates. In a preferred embodiment, the methods of the invention are used to synthesize the peptide having the above formula wherein X is an acetyl group and Z is an amide group. Techniques for addition of such "X" and "Z" groups are well known to those of skill in the art.

In a preferred method, T-1249 and T-1249-like peptides and intermediates can be purified using any non-silica based column packing (for maximization of loading capacity) including but not limited to zirconium-based packings, poly-styrene, poly-acrylic or other polymer based packings which are stable at high and low pH ranges. For example, among the non-silica-laded column packing exhibiting a broad pH range that includes pH values greater than seven are ones sold by Tosohaas (Montgomeryville, Pa.). Columns packed with such material can be run in low, medium or high pressure chromatography according to standard techniques well known in the art.

The Examples presented in Section 9, below, demonstrate the successful synthesis of T-1249 peptides via coupling of peptide intermediates described, below, in Section 5.2.

5.2 PEPTIDE INTERMEDIATES

The present invention encompasses, but is not limited to, peptide fragment intermediates of T-1249 and T-1249-like peptides with specific amino acid sequences as listed in Table 1 above, and the groups of peptide fragment intermediates listed in Table 2. Such peptide intermediates, especially in groups as listed in Table 2, below, can be utilized to produce T-1249 and T-1249 like peptides.

Any one or more of the side-chains of the amino acid residues of peptide fragments listed in Table 1 or 2 may be protected with standard protecting groups such as t-butyl (t-Bu), trityl (trt) and t-butyloxycarbonyl (Boc). The t-Bu group is the preferred side-chain protecting group for amino acid residues Tyr(Y), Thr(T), Ser(S), Glu(E) and Asp(D); the trt group is the preferred side-chain protecting group for amino acid residues, Gln(Q) and Asn(N); and the Boc group is the preferred side-chain protecting group for amino acid residues Lys(K) and Trp(W).

Preferably, the Gln(Q) residues of the peptide fragments of the invention are protected with trityl (trt) groups. However, if lower solubility of any of the peptide fragments of the invention in organic solvents is desired, the trityl protecting groups may be eliminated from any one or more of the glutamine residues of the fragments.

Preferably, the Asn(N) residues of each peptide fragment of the invention are protected. In addition, it is preferred that the Trp(W) residues are protected with a Boc group.

Protected peptide fragments according to peptide formulas 1–5 listed in Table 1 above include, but are not limited to, the compounds listed in Table 3 below.

TABLE 3

| Peptide Formula No. | Formula | | Corresponding Numbered Amino Acid Sequence of T-1249 (SEQ ID NO:1) |
|---|---|---|---|
| 1 | Ac-WQEWEQKITALL-COOH | (SEQ ID NO:2) | 1–12 |
| 2 | FMOC-EQAQIQQEKNEYEL-COOH | (SEQ ID NO:3) | 13–26 |
| 3 | FMOC-QKLDKWASLWEW-COOH | (SEQ ID NO:4) | 27–38 |
| 4a | FMOC-QKLDKWASLWEWF-NH$_2$ | (SEQ ID NO:5) | 27–39 |
| 4b | NH$_2$-QKLDKWASLWEWF-NH$_2$ | (SEQ ID NO:5) | 27–39 |
| 5a | FMOC-EQAQIQQEKNEYELQKLDKWASLWEWF-NH$_2$ | (SEQ ID NO:6) | 13–39 |
| 5b | NH$_2$-EQAQIQQEKNEYELQKLDKWASLWEWF-NH$_2$ | (SEQ ID NO:6) | 13–39 |

Any one or more of the side-chains of the amino acid residues of the peptides listed in Table 3 above may be protected with standard side-chain protecting groups such as tBu, trt and Boc, as described above. Representative syntheses of peptides from Table 3 are presented in Sections 7 and 8 below, which utilize the general techniques discussed in Section 5.3, below.

5.3 PEPTIDE SYNTHESIS

As discussed above, some of the individual peptide fragments of the invention are preferably made using solid phase synthesis techniques, while other peptides of the invention are preferably made using a combination of solid phase and solution phase synthesis techniques, said syntheses culminating in the production of T-1249 or T-1249-like peptides as described herein. However, it will be understood that the peptide fragments of the invention may be synthesized or prepared by techniques well known in the art. See, for example, Creighton, 1983, Proteins: Structures and Molecular Principles, W. H. Freeman and Co., NY, which is incorporated herein by reference in its entirety.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few.

In yet another embodiment of the invention, T-1249 and T-1249-like peptides comprising the sequences described above may be synthesized with additional chemical groups present at their amino and/or carboxy termini, such that, for example, the stability, reactivity and/or solubility of the peptides is enhanced. For example, hydrophobic groups such as carbobenzoxyl, dansyl, acetyl or t-butyloxycarbonyl groups, may be added to the peptides' amino termini. Likewise, an acetyl group or a 9-fluorenylmethoxy-carbonyl group may be placed at the peptides' amino termini. (See "X" modification of T-1249, described above.) Additionally, the hydrophobic group, t-butyloxycarbonyl, or an amido group may be added to the peptides' carboxy termini. Similarly, a para-nitrobenzyl ester or benzyl ester group may be placed at the peptides' carboxy termini. (See "Z" modification of T-1249, described above.) Techniques for introducing such modifications are well known to those of skill in the art.

Further, T-1249 and T-1249-like peptides may be synthesized such that their steric configuration is altered. For example, the D-isomer of one or more of the amino acid residues of the peptide may be used, rather than the usual L-isomer.

Still further, at least one of the amino acid residues of the peptides of the invention may be substituted by one of the well known non-naturally occurring amino acid residues. Alterations such as these may serve to increase the stability, reactivity and/or solubility of the peptides of the invention.

Any of the T-1249 or T-1249-like peptides may be synthesized to additionally have a macromolecular carrier group covalently attached to its amino and/or carboxy termini. Such macromolecular carrier groups may include, for example, lipid-fatty acid conjugates, polyethylene glycol, carbohydrates or additional peptides. The "X" modification of T-1249 described above may therefore additionally represent any of the above macromolecular carrier groups covalently attached to the amino terminus of a peptide, with an additional peptide group being preferred. Likewise, the "Z" modification of T-1249 described above may additionally represent any of the macromolecular carrier groups described above.

Preferably, the peptide fragments of the present invention are synthesized by solid phase peptide synthesis (SPPS) techniques using standard FMOC protocols. See, e.g., Carpino et al., 1970, J. Am. Chem. Soc. 92(19):5748–5749; Carpino et al., 1972, J. Org. Chem. 37(22):3404–3409. In a preferred embodiment, the solid phase synthesis of the peptide fragments of the present invention is carried out on super acid sensitive solid supports which include, but are not limited to, 2-chlorotrityl chloride resin (see, e.g., Barlos et al., 1989, Tetrahedron Letters 30(30):3943–3946) and 4-hydroxymethyl-3-methoxyphenoxybutyric acid resin (see, e.g., Seiber, 1987, Tetrahedron Letters 28(49):6147–6150, and Richter et al., 1994, Tetrahedron Letters 35(27):4705–4706). Both the 2-chlorotrityl chloride and 4-hydroxymethyl-3-methoxyphenoxy butyric acid resins may be purchased from Calbiochem-Novabiochem Corp., San Diego, Calif.

General, non-limiting procedures for production and loading of resins which can be utilized in solid phase peptide synthesis are described herein. In addition, the examples present in Section 6, below, describe exemplary resin preparations.

Resin loading can be performed, for example, via the following techniques: The resin, preferably a super acid sensitive resin such as 2-chlorotrityl resin, is charged to the reaction chamber. The resin is washed with a chlorinated solvent such as dichloromethane (DCM). The bed is drained and a solution of 0.5–1.5 equivalents of an amino acid with an 0.2 to 0.5 excess of diisopropylethylamine (DIEA) in about 8–10 volumes of dichloroethane (DCE) is added. The N-terminus of the amino acid should be protected, preferably with Fmoc, and the side chain of the amino acid should be protected where necessary or appropriate. The mixture is agitated with nitrogen bubbling for 2–24 hours.

It should be noted that a chlorinated solvent such as DCM or DCE is desired for adequate swelling of the 2-chlorotrityl resin.

After agitation, the bed is drained and washed with DCM. The active sites on the resin are endcapped with a 9:1 MeOH:DIEA solution for about 20–30 minutes. The bed is drained, washed four times with DCM and dried with a nitrogen purge to give the loaded resin.

Fmoc is the preferred protecting group for the N-terminus of the amino acid. Depending on which amino acid is being loaded, its side chain may or may not be protected. For example, when tryptophan (Trp) is loaded, its side chain should be protected with Boc. However, it is not necessary to protect the side-chain of leucine (Leu). Preferably, glutamic acid (Glu), aspartic acid (Asp), threonine (Thr) and serine (Ser) are protected as t-butyl ethers or t-butyl esters, and tryptophan (Trp) and lysine (Lys) are protected as t-butoxycarbonyl carbamates (Boc). The amide side-chain of asparagine (Asn) and glutamine (Gln) may or may not be protected with trityl groups.

The Fmoc-protected amino acids used in loading the resin and in peptide synthesis are available, with or without side-chain protecting groups as required, from multiple vendors, including Senn or Genzyme. As an alternative to the above procedure, the resin may be purchased already loaded with the appropriate amino acid.

The Examples presented in Section 6, below, describe exemplary resin preparations.

Solid phase peptide synthesis techniques can be performed as, for example, according to the following, non-limiting techniques: The loaded resin is added to the reaction chamber and conditioned with a solvent, preferably methylene chloride (DCM; at preferably about 10 vol.) with nitrogen agitation or stirring for about 15 minutes to swell the resin beads. DCM is required for adequate swelling of the 2-chlorotrityl resin. The resin volume will increase 3–6 fold in the reaction chamber as the beads swell and the active sites unfold and become accessible to reaction. After the resin is swelled, the solvent is drained from the reaction chamber.

Removal of the Fmoc (9-fluroenyl-methyloxycarbonyl) protecting group from the terminal amine or the resin can be accomplished by treating the resin with 2 aliquots of a 20% solution of piperidine in N-methyl-2-pyrrolidinone (NMP) for about ten minutes each. The volume of the 20% solution of piperidine in NMP required for each aliquot will depend on the scale of the reaction being run. The resin is then washed 5–7 times with aliquots of NMP (about10 vol.) to remove the Fmoc by-products (i.e., dibenzofulvene and its piperidine adduct) and residual piperidine.

A chloranil test may be used to determine if the removal of residual pyridine is complete. The chloranil test solution is prepared by adding a drop of a saturated solution of chloranil in toluene to about 1 mL of acetone. The NMP washings may be tested by adding a drop of the washing to the chloranil test solution. A blue or violet color is a positive indication for the presence of secondary amine, indicating that residual piperidine is still present. The NMP washing is repeated until the blue or violet color is no longer observed.

Meanwhile, the subsequent amino acid in the sequence to be added to the resin is activated for reaction at its carboxy terminus. The amine terminus of each amino acid should be protected with Fmoc. Depending on which amino acid is being added, its side chain may or may not be protected. Preferably, the side-chains of tyr(Y), Thr(T), Ser(S), Glu(E) and Asp(P) are protected with t-Bu, the side-chains of Gln(Q) and Asn(N) are protected with trt, and the side-chains of Lys(K) and Trp(w) are protected with Boc. It is not necessary for the side-chains of Leu or Ile to be protected.

The amino acid can be activated as follows. The Fmoc-protected amino acid (1.5 eq), 1-hydroxybenzotriazole hydrate (HOBT) (1.5 eq), and diisopropyl-ethylamine (DIEA) (1.5 eq) are dissolved in a polar, aprotic solvent such as N-methyl pyrrolidinone (NMP), dimethyl formamide (DMF) or dimethyl acetamide (DMAC) (about 7.5 vol.) at room temperature. The solution is chilled to 0–5° C., and then O-benzotriazol-1-yl-N,N,N',N'-tetramethyluronium hexafluorophosphate (HBTU) or O-benzotriazol-1-yl-tetramethyltetrafluoroborate (TBTU) (1.5 eq) is added followed by stirring for 5–15 minutes to dissolve. It is important that activation is carried out at 1–5° C. to minimize racemization of the amino acid. The HBTU is the last reagent added to the cold solution since activation and racemization cannot take place in its absence.

The solution of activated amino acid is charged to the drained resin, washing in with DCM (approximately 2.5 vol). Note that activation of the amino acid is carried out in NMP due to the insolubility of HBTU in DCM. However, DCM is added to the reaction at this point to maintain adequate swelling of the resin beads. The reaction is agitated with $N_2$ bubbling for about 1 hour at 20–30° C. Coupling completion may be monitored with a qualitative ninhydrin test as described below.

To check for completion of the reaction using the qualitative ninhydrin test, a 2–20 mg sample of the resin can be withdrawn and washed clean with methanol. To the sample is added 3 drops of a 76% solution of phenol in ethanol, 4 or 5 drops of a 0.2 mM KCN solution in pyridine, and 3 drops of a 0.28 M solution of ninhydrin in ethanol. The sample is diluted with ethanol to a volume of about 0.5 mL and placed in a heat block at about 75° C. for 5–10 minutes. A blue or violet color is a positive indication for the presence of free amines, indicating that the reaction is not yet complete. The sample can be diluted further to a volume of about 3 mL to more easily gauge the degree of color change in the concentrated sample.

If a positive ninhydrin test is observed after one hour, the coupling reaction is continued for an additional hour. If the positive ninhydrin test persists after 3 hours, the resin is drained, washed one time in approximately 10 volumes of NMP, and the coupling reaction is repeated using 0.5–1 equivalent of activated amino acid.

If the resin is to be stored overnight between coupling cycles, the resin bed may be drained and covered with NMP under a nitrogen blanket. Alternatively, the bed may be drained, stored under a nitrogen blanket, then conditioned with a DCM wash prior to proceeding with the next coupling cycle. If the completed fragment is to be stored overnight prior to cleavage, the resin bed should be washed free of NMP with IPA because significant Fmoc deprotection can occur in NMP.

After the coupling is judged complete, the resin is drained and washed with 3 aliquots (approximately 10 vol.) of NMP.

The cycle is repeated for subsequent mers (i.e., amino acids) of the peptide fragment. Following the final coupling reaction, the resin is washed with 4 aliquots (about 10 vol.) of NMP, then with 2 aliquots (approximately 10 vol.) of DCM and 2 IPA. The resin-bound peptide may be dried with a nitrogen purge or in an oven.

Peptides synthesized via solid phase synthesis techniques can be cleaved and isolated according to, for example, the following non-limiting techniques: The peptide may be cleaved from the resin using techniques well known to those skilled in the art. For example, solutions of 1% or 2% trifluoroacetic acid (TFA) in DCM or a combination of a 1% and a 2% solution of TFA in DCM may be used to cleave the peptide. Acetic acid (HOAC), hydrochloric acid (HCl) or formic acid may also be used to cleave the peptide. The specific cleavage reagent, solvents and time required for cleavage will depend on the particular peptide being cleaved. After cleavage the cleavage fractions are subjected to standard work-up procedures to isolate the peptide. Typically, the combined cleavage fractions are concentrated under vacuum, followed by reconstitution with polar aprotic or polar aprotic solvents such as ethanol (EtOH), methanol (MeOH), isopropyl alcohol (IPA), acetone, acetonitrile (ACN), dimethyl formamide (DMF), NMD, DMAC, DCM, etc., followed by precipitation or crystallization with anti-solvent such as water or hexanes, and collection by vacuum filtration. Alternatively, the product may be triturated with organic solvents or water after isolation of the peptide.

The Examples presented in Sections 7.1–7.6 below, present solid phase syntheses of peptide intermediates as shown in Tables 1, 2 and/or 3.

For synthesis of full length T-1249 peptides, the peptide intermediates of Table 1, above, can be coupled together to yield the T-1249 peptide. For example, the groups of peptide intermediates listed in Table 2, above, can be coupled together to produce T-1249 full-length peptide. Representative examples of the synthesis of full-length T-1249 from intermediate peptide fragments are presented in Section 9, below, and are depicted schematically in FIG. 1.

In certain embodiments, a three fragment approach for synthesis of T-1249 can be followed. A "three fragment approach" synthesis refers to a T-1249 synthesis scheme which begins with three T-1249 intermediate peptide fragments that are synthesized and coupled using solid and liquid phase synthesis techniques into a full-length T-1249 peptide. Intermediate peptide fragment groups 1, 2, 3 and 4 shown in Table 2, above, represent preferred groups. FIG. 1 depicts an exemplary three fragment approach which utilizes Table 2 peptide intermediate Group 1 to synthesize full-length T-1249. For this group, it is noted that amino acid residue 39 (the T-1249 carboxy 1-terminal amino acid residue) is introduced individually during the fragment coupling process. The culmination of the T-1249 synthesis scheme shown in FIG. 1 is demonstrated in the example presented in Section 9.1.

Solution phase peptide synthesis techniques well known to those of skill in the art may be utilized for synthesis of the peptide intermediate fragments of the invention. The Examples presented in Section 8 describe exemplary solution phase peptide synthesis of peptide intermediates listed in Tables 1, 2, and/or 3. For example, among the non-silica-laded column packing exhibiting a broad pH range that includes pH stability values at high or low pH are sold by Tosohaas (Montgomeryville, Pa.).

6. EXAMPLE

Resin Syntheses

6.1. Preferred Exemplary Method for Loading Amino Acids onto 2-CTC Resin

The air sensitive 2-chlorotritylchloride resin (Senn Chemicals, Lot A 3573, 1 eq, 12.0 mmol, 10.0 g) is added to a 250 mL round bottom flask and immediately treated with a prepared solution of FmocLeuOH (1.0 eq., 12 mmol, 4.24 g) and Diisopropylethylamine (5 eq., 60.0 mmol, 5.20 mL) in DCM (10 vol, 100 mL). The slurry is capped and stirred for 3 hours. The solvent is removed by filtration and the resin is washed with DCM (5 vol, 50 mL). The remaining active sites on the resin are end-capped by treating resin with 9:1 MeOH:DIEA (5 vol, 5.0 mL DIEA and 45 mL MeOH) for 30 minutes. The solvent is removed and the resin is washed with 3×5 volumes of DCM. The resin is dried to constant weight affording 13.2 g of loaded resin with a calculated loading of 0.98 mmol FmocLeuOH per gram.

This Method can also be used for Loading FmocTrp(Boc)OH onto 2-CTC resin.

Described herein, in Sections 6.2–6.3, are examples in which chlorotrityl chloride resins were substituted with amino acids which can be utilized in conjunction with solid phase synthesis of the peptides and peptide intermediates described herein. All of the peptides and peptide fragments of the present invention may be synthesized by solid phase peptide synthesis (SPPS) using the loading procedures described in Sections 6.2 and 6.3 below.

6.2 Preparation of Fmoc-Trp(Boc)-2-Chlorotrityl Resin

| 6.2 Preparation of Fmoc-Trp(Boc)-2-Chlorotrityl Resin | | | | | |
|---|---|---|---|---|---|
| Materials: | MW | eq | mmoles | grams | mL |
| 2-Chlorotritylchloride resin | — | 1.0 | 25 | 25 | — |
| Fmoc-Trp(Boc)-OH | — | 526.60 | 1.5 | 37.5 | 19.7 |
| Diisopropylethyl amine (DIEA) | 129.25 | 1.7 | 42.5 | 5.5 | 7.4 |
| Dichloroethane (DCE) | — | — | — | — | 250 |
| Dichloromethane (DCM) | — | — | — | — | 6 × 250 |
| 9:1 Methanol:DIEA | — | — | — | — | 200 |

Procedure

The 2-chlorotrityl chloride resin (25 g, 1 eq.) was charged to a 500 mL peptide chamber and washed with 250 mL of DCM. The bed was drained and a solution of the Fmoc-Trp(Boc)-OH (1.5 eq) and the DIEA (1.7 eq) in 10 volumes of DCE was added. The mixture was agitated with nitrogen bubbling for 2 hrs.

The bed was drained and washed with 250 mL DCM. The active sites on the resin were end-capped with 200 mL of a 9:1 MeOH:DIEA solution for 20 minutes. The bed was drained, washed with 4×250 mL of DCM, and dried with a nitrogen purge to give 34.3 g of loaded resin.

Quantitative HPLC analysis was performed by cleaving the Fmoc-amino acid from the resin and assaying versus a standard. HPLC assay of the material showed a loading of the resin at 0.68 mmol/g.

| Column: | Phenomenox Jupiter C18; 300 Å; 5μ |
|---|---|
| Flow Rate: | 1 mL/min |
| Detection: | UV at 260 nm |
| Mobile Phase: | A: 0.1% aqueous TFA |
| | B: 0.1% TFA in acetonitrile |
| | 65% B isocratic |
| Retention Phase: | Approximately 14 minutes |

6.3 Preparation of Fmoc-Leu-2-Chlorotrityl Resin

6.3 Preparation of Fmoc-Leu-2-Chlorotrityl Resin

| Materials: | MW | eq | mmoles | grams | mL |
|---|---|---|---|---|---|
| 2-Chlorotritylchloride resin | — | 1.0 | 250 | 250 | — |
| FmocLeuOH | 353.42 | 1.5 | 375 | 132.5 | — |
| Diisopropylethyl amine (DIEA) | 129.25 | 1.7 | 425 | 55 | 75 |
| Dichloroethane (DCE) | — | — | — | — | 2000 |
| Dichloromethane (DCM) | — | — | — | — | 6 × 1500 |
| 9:1 Methanol:DIEA | — | — | — | — | 1500 |

Procedure

The resin was charged to a 3 L peptide chamber and washed with 1.5 DCM. The bed was drained and a solution of the FmocLeuOH (1.5 eq) and the DIEA (1.7 eq) in 8 volumes of DCE was added. The mixture was agitated with nitrogen bubbling for 2 hrs.

The bed was drained and washed with 1.5 L DCM. The active sites on the resin were end-capped with 1.5 L of a 9:1 MeOH:DIEA solution for 30 minutes. The bed was drained, washed with 4×1.5 L of DCM, and dried with a nitrogen purge to give 345 g of loaded resin.

Quantitative HPLC analysis was performed by cleaving the Fmoc-amino acid from the resin and assaying versus a standard. HPLC assay of the material showed a loading of the resin at 0.72 mmol/g.

| Column: | Phenomenox Jupiter C18; 300 Å; 5μ |
|---|---|
| Flow Rate: | 1 mL/min |
| Detection: | UV at 260 nm |
| Mobile Phase: | A: 0.1% aqueous TFA |
| | B: 0.1% TFA in acetonitrile |
| | 65% B isocratic |
| Retention Phase: | Approximately 8 minutes |

7. EXAMPLE

Solid Phase Synthesis of Peptides

Presented below, in Sections 7.1–7.6, are examples of the solid phase synthesis of peptide intermediates as listed in Tables 1, 2, and/or 3.

7.1 Preferred Method for Solid Phase Peptide Synthesis (SPPS); General Procedure A SPPS chamber is charged FmocLeu-resin (1 eq). The resin is conditioned in 5% piperidine DCM (7.5 vol) with a nitrogen purge for 15–30 minutes. The solvent is drained and the resin is treated with 2×20% piperidine in NMP (5 volumes) for 30 minutes to remove the Fmoc protecting group. After the second 20% piperidine/NMP treatment, the resin is washed with 5–7× NMP (5 vol) to a negative choranil test.

Meanwhile, the subsequent amino acid (1.5 eq), HOBT (1.5 eq) and DIEA (1.5 eq) are combined in 3:1 NMP/DCM (10 vol), allowed to fully dissolve at room temperature and cooled to 0° C. HBTU is added, the solution is stirred for 10–15 minutes to dissolve the solid then added to the resin. The suspension is agitated with stirring under a nitrogen atmosphere for 1–3 hours. Coupling completion is monitored with a qualitative ninhydrin test. If the reaction is incomplete after 3 h (positive ninhydrin test persists) the reactor should be drained and a recoupling should be performed with a fresh solution of activated amino acid (0.5 eq). Normally after 30 min-1 h of recoupling a negative ninhydrin test is obtained. This cycle is repeated for the remaining amino acids in the fragment. As the fragment builds, the solvent volumes used in the washes may need to be increased from 5 volumes. In the case of AcAA1-12OH end capping with Acetic anhydride was carried out by treating de-Fmoced (HAA1-12-resin) with pyridine (5 eq.) then acetic anhydride (5 eq.) in 3:1 NMP/DCM (10 vol). Following the final coupling, the resin is washed with 3×5–8 volumes of NMP then 2×10 volumes of DCM and dried to constant weight in a vacuum oven at 40° C.

7.2 Preferred Methods for Cleavage of the Peptide from Resin

The methods below describe the cleavage of peptide AcAA1-12OH from the resin. However, the same methods may be used for cleavage of other peptide fragments of the present invention.

Method A: Use of HOAc

The resin (1 g, 0.370 mmol) was treated with mixture of AcOH/MeOH/DCM (5:1:4, 20 vol, 20 mL) with nitrogen agitation for 1.5 h and the solution was transferred to a round bottom flask, stirred, and treated with water (20 vol). The resulting white slurry was concentrated (rotavap, 40° C. bath) to remove DCM and the product collected by filtration. Drying to a constant weight affords 0.69 g (74%) of AcAA1-12OH in 87A % purity. A second treatment of the resin as above provided an additional 0.08 g (8.5%) of AcAA1-12OH of less pure material (83 Area %) suggesting a desired reaction time of slightly >1.5 hr.

Method B: Use of TFA

The resin (1 wt., 20 g) is washed with 5–6×1.7 volumes of 1% TFA in DCM, 3–5 minutes each. The 1% TFA/DCM washes are collected in a flask containing pyridine (1:1 volume ratio with the TFA in the wash). The product containing washes are combined (600 mL, 30 vol) and the DCM is removed by distillation to a minimum pot volume (~⅓ the original volume). The vacuum is adjusted to maintain a pot temperature of 15–25° C. Ethanol (6.5 vol) is added and the distillation is continued until the DCM is removed (as determined by an increase in the temperature of the distillate). Again the vacuum is adjusted to maintain a pot temperature of 15–20° C. The final pot volume should be ~8–9 volumes. The solution is cooled to 5–10° C. and water (6.5 vol) is added over 30 minutes to precipitate the AcAA1-12OH. The solid is collected by vacuum filtration and washes with water (2–3 vol). The slurry is stirred at 0–5° C. for 30 minutes, the solids are collected by vacuum filtration and dried to constant weight to give 16.80 g of AcAA1-12OH in 90% yield and 84 Area % (A %) purity.

7.3 Preferred Method for Rework of AcAA1-12OH

Heat AcAA1-12OH (257-21-1, 3.00 g) in 70 mL methanol (23.3 volumes) at 65° C. with stirring for 3 h. Cool to room temperature and stir overnight. Suction filtration and drying to constant weight in vacuum oven (40° C.) gave 2.43 g (81%) in 90A %.
HPLC Conditions Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 uL into a 20 uL loop.

7.4 SPPS of FmocAA13-26OH and Cleavage from the Resin

SPPS of FmocAA13-26 was carried out as described above starting with 6.5 g of FmocLeuOResin loaded at 1.02 mmol/g. Cleavage method A or B is acceptable (169/137, 60% yield, 85A %).

7.5 Preferred Rework Procedure for FmocAA13-26OH

FmocAA13-26OH (3.60 g, 85A %) was heated in 15 mL (5 vol) acetonitrile at 78° C. The slurry was treated with additional solvent until the solids dissolved (total 0.6 mL). The solution was allowed to cool to room temperature and stirred 7 h. Suction filtration and drying to a constant weight provided 2.6 g (72%) of FmocAA13-26OH in 95 A %.
HPLC Conditions Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 uL into a 20 uL loop.

7.6 SPPS of FmocAA27-38OH and Cleavage from the Resin

SPPS of FmocAA27-38OH was carried out as described above starting with log of FmocTrp(Boc)OR loaded at 0.75 mmol/g. Cleavage method B was used (169/120/1, 78% yield, 87.9A %).
HPLC Conditions Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 $\mu$L into a 20 $\mu$L loop.

8. EXAMPLE

Solution Phase Synthesis of Peptide Fragments

Presented below, in Sections 8.1–8.4, are examples of the solution phase synthesis of peptide intermediates as listed in Tables 1, 2, and/or 3.

8.1 Preparation of Fragment Fmoc-AA27-39-NH$_2$ by Solution Phase Coupling of HPheNH$_2$ to Fmoc-AA27-38OH FmocAA27-39NH$_2$ may be prepared by converting the carboxyl terminus of FmocAA27-38OH to an activated HOBT or HOAT ester using HBTU or TBTU and HOBT or HOAT, respectively, in the presence of DIEA and phenylalanine amide. The reaction is run in a polar, aprotic solvent such as DMF or NMP at 0 to 25C. At completion of the reaction, alcohol or a water miscible solvent and/or water are added to precipitate FmocAA27-39NH$_2$.

EXAMPLE

FmocAA27-38OH (169-120-1, 5.40 g, 1.98 mmol, 1.00 eq.), HPheNH$_2$ (Bachem, 0.390 g, 2.38 mmol, 1.20 eq.), HOBT.H$_2$O (0.330 g, 2.16 mmol, 1.10 eq.) were dissolved in NMP (54 mL, 10 vol), treated with DIEA (0.16 mL, 0.921 mmol, 1.10) and stirred at room temperature until dissolved (ca. 30 min). The solution was cooled using an ice bath (internal T=2–3° C.) and HBTU (0.827 g, 2.18 mmol, 1.10 eq.) was added in one portion, stirred 1 h, then overnight. The reaction can be monitored by TLC (uv, 10% MeOH/ DCM, SM mid Rf, product above). Addition of methanol (54 mL, 10 vol) then water (54 mL, 10 vol) dropwise over a 1 h period formed a free-flowing solid which was stirred an additional 2 h then collected by filtration. The filtercake was washed with 1:1 water/methanol (2×25 mL). Drying overnight in vacuum oven at 40° C. afforded 5.30 g (93%) FmocAA27-39NH2 in 81A %. HPLC analysis also showed that <0.2% of starting material FmocAA27-38OH was present. ES pos=2871 (MH+), ES neg=2869 (M-1). Average MW=2870.
HPLC Conditions Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 $\mu$L into a 20 $\mu$L loop.

8.2 Preparation of Fragment HAA27-39NH$_2$ by Removal of FMOC Group

The Fmoc protecting group of Fmoc AA27-39NH$_2$ is removed using a base such as piperidine or potassium carbonate in organic solvents such as DCM, DMF, NMP, methyl t-butyl ether (MTBE), hexane, or mixtures thereof.

EXAMPLE

FmocAA27-39OH (257-25-1, 4.00 g, 1.39 mmol) was slurried in 40 mL (10 vol) of MTBE and 10 mL (2.5 vol) of heptane then treated with piperidine (0.75 mL, 8.34 mmol, 5.5 eq.). The slurry was stirred 12 h at which point 0.5% starting material remained (HPLC) and 20 mL (5 vol) of heptane was added. The free-flowing slurry was stirred 1 h, then isolated by suction filtration and washed 3×7 mL (2 vol each wash) with 1:1 MTBE/Heptane and dried in a vacuum oven at 40° C. until constant weight affording 3.55 g (96%) of 257-40-1 in 83A % purity.
HPLC Conditions Vydac C8, Cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 uL into a 20 uL loop.

8.3 Preparation of Fragment Fmoc-AA13-39-NH$_2$ by Solution-Phase Coupling of Fragments Fmoc-AA13-26OH and HAA27-39NH$_2$ FmocAA13-39NH$_2$ is prepared by converting the carboxyl terminus of FmocAA13-26OH to an activated HOBT or HOAT ester using HBTU or TBTU and HOBT or HOAT, respectively, in the presence of DIEA and HAA27-39NH$_2$. The reaction is run in a polar, aprotic solvent such as DMF or NMP at 0 to 25C. At completion of the reaction, alcohol or a water miscible solvent and/or water are added to precipitate FmocAA13-39NH$_2$.

EXAMPLE

FmocAA13-26OH (257-41-1, 3.00 g, 0.8417 mmol, 1 eq.), HAA27-39NH$_2$ (2.23 g, 0.8417 mmol, 1 eq.), HOBT hydrate (0.135 g, 0.884 mmol, 1.05 eq.) were dissolved in DMF (25 mL, 30 min.),cooled with an ice bath and treated with DIEA (0.23 mL, 1.33 mmol, 1.50 eq.) then HBTU (0.335 g, 0.884 mmol, 1.05 eq.) and stirred. After 1 h the reaction was 90% complete based on loss of starting materials (HPLC) and was warmed to room temperature. After 4 h, additional HBTU (0.150 g, 0.395 mmol, 0.5 eq.) was added, and the reaction was stirred overnight. Methanol (50 mL), then water (50 mL) was added dropwise causing gumming which solidified to a slurry after stirred 16 h at ambient temperature. The solid was collected by filtration, washed with 2×20 mL 1:1 MeOH: water and drying to constant weight giving 5.18 g (99%) of FmocAA13-39NH2 in 60A % purity. The solid 5A % each of acid and amine starting materials.

HPLC Conditions

Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 uL into a 20 uL loop.

8.4 Preparation of Fragment HAA13-39NH$_2$ by Removal of Fmoc Group

The FMOC protecting group of FmocAA13-39NH$_2$ is removed using a base such as piperdine or potassium carbonate in organic solvents such as DCM, DMF, NMP, MTBE, hexane, or mixtures thereof.

EXAMPLE

FmocAA13-39OH (257-43-1, 0.500 g, 0.0810 mmol, 1 eq.) was slurried in 9 mL (18 vol) of 2:1MTBE/Heptane for 30 minutes then treated with piperidine (40 µL, 0.404 mmol, 5 eq.). The slurry was stirred 2 h at which point 40% starting material remained (HPLC). Additional MTBE (3 mL, 6 vol) and piperidine (20 µL, 2.5 eq.) were added and the slurry stirred until <1% starting material remained (16 h). The reaction slurry was suction filtered, washed with 2×5 mL of 1:1 MTBE/heptane and dried to a constant weight affording 0.40 g (90%) in ca. 60–70A %.

HPLC Conditions

Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 µL into a 20 µL loop.

9. EXAMPLE

Synthesis of Full Length T-1249 Peptides

Presented herein, in Sections 9.1–9.2, below, are examples of the utilization of the peptide intermediate fragments to produce full length T-1249 peptides.

The Example presented in this Section demonstrates the successful coupling of solid phase and solution phase synthesis techniques to produce a full-length T-1249 peptide from peptide intermediate fragments.

9.1 Preparation of Fragment AcAA1-39NH$_2$ by Solution-phase Coupling of AcAA1-12OH with HAA13-39NH$_2$ The synthesis route described here represents the culmination of the T-1249 three fragment approaches schematically depicted in FIG. 1. AcAA1-39NH$_2$ may be prepared by converting the carboxyl terminus of AcAA1-12OH to an activated HOBT or HOAT ester using HBTU or TBTU and HOBT or HOAT, respectively, in the presence of DIEA and HAA13-39NH$_2$. At completion of the reaction, alcohol or a water miscible solvent and/or water are added to precipitate AcAA1-39NH$_2$.

EXAMPLE

HAA13-39 (257-32-2, 0.409 g, 0.0685 mmol, 1 eq.), AcAA1-12OH (257-21-1, 0.174 g, 0.0685 mmol, 1 eq.) and HOBT hydrate (0.013 g, 0.0822 mmol, 1.20 eq.) were dissolved in DMF (6.0 mL, 12 vol, 30 min.). The solution was cooled with an ice bath and DIEA (18 µL, 0.1028 mmol, 1.5 eq.) followed by HBTU (0.031 g, 0.0822 mmol, 1.20 eq.). After stirring 4 h at 0C, water (6 mL) was added dropwise. The resulting slurry was stirred 1 h then isolated by suction filtration. Drying overnight in a vacuum oven at 40° C. gave 0.545 g (94%) of 257-33-1 in ca. 50A %.

HPLC Conditions

Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 µL into a 20 µL loop.

9.2 Preparation of T-1249 Side by Side-chain Deprotection of AcAA1-39NH$_2$

The Example presented in this Section demonstrates the successful coupling of solid and liquid phase synthesis techniques to produce a T-1249 peptide from peptide intermediate fragments. In particular, the synthesis route described here represents the final deprotection step of the T-1249 three fragment approach shown in FIG. 1. Preferably, the side-chain protecting groups of AcAA1-39NH$_2$ are removed by acidolysis using 95/5 trifluoroacetic acid/water and up to 5 wt/vol % of a carbocation scavenger such as dithiothreitol, ethane dithiol or cystine. The crude T-1249 is precipitated from the deprotection solution by addition of an ether such as MTBE, diethyl ether or diisopropyl ether.

EXAMPLE

AcAA1-39NH$_2$ (257-33-1, 0.120 g) was treated with 1.5 mL of a freshly prepared solution of TFA:DTT:water (95:5:5) and stirred at room temperature for 4 h. MTBE (approximately 3 mL) was added and the precipitate collected by vacuum filtration. The fine powder was dried in the vacuum oven overnight. This material was dissolved in 3 mL of 50% Acetonitrile/water containing 1% HOAc and allowed to stand for 15 hours to allow for decarboxylation of the indole side-chain of the tryptophans. The solution was analyzed directly and found to co-eluted with authentic T-1249. Approximate purity was 60% by HPLC.

HPLC Conditions

Vydac C8, cat. No. 208TP54, 5 u, 300 A, 0.9 mL/min., 280 nm. A: 0.1% TFA/water, B: A mixture of 80% I-PrOH/ 20% Acetonitrile and 0.1% TFA. 60–80% B/30 min. Typical sample preparation: Dissolve 1 mg in 0.10 mL NMP, dilute with 1 mL Acetonitrile. Inject 20 µL into a 20 µL loop.

What is claimed is:

1. A method for synthesizing a peptide of the formula X-WQEWEQKITALLEQAQIQQEKNEYELQKLDKWASLWEWF-Z (SEQ ID NO:1) comprising reacting a side-chain protected peptide of the formula EQAQIQQEKNEYELQKLDKWASLWEWF-Z (SEQ ID NO:6) to yield a side-chain protected peptide of the formula
X-WQEWEQKITALLEQAQIQQEKNEYELQKLDKWASLWEWF-Z (SEQ ID NO:1);
wherein the amino terminus of EQAQIQQEKNEYELQKLDKWASLWEWF-Z (SEQ ID NO:6) is deprotected with a side-chain protected peptide of the formula X-WQEWEQKITALL-COOH (SEQ ID NO:2);
wherein X is a protecting group, an acetyl group or a macromolecular carrier group; and
whereto Z is a protecting group, an amido group, or a macromolecular carrier group.

2. The method of claim 1 wherein X is a protecting group selected from the group consisting of 9-fluoroenylmethoxycarbonyl (Fmoc), t-butyl (t-Bu), trityl (trt), t-butyloxtycarbonyl (Boc), carbobenzoxyl, dansyl and a para-nitrobenzyl ester group.

3. The method of claim 1 wherein Z is a protecting group selected from the group consisting of 9-fluoroenylmethoxycarbonyl (Fmoc), t-butyl (t-Bu), trityl (trt), t-butyloxycarbonyl (Boc), carbobenzoxyl, dansyl and a para-nitrobenzyl ester group.

4. The method of claim 1 wherein X is a macromolecular carrier group selected from the group consisting of lipid-fatty acid conjugates, polyethylene glycol and carbohydrates.

5. The method of claim 1 wherein Z is a macromolecular carrier group selected from the group consisting of lipid-fatty acid conjugates, polyethylene glycol and carbohydrates.

6. The method of claim 1 which further comprises the step of deprotecting the side chains of the side-chain protected peptide of the formula X-WQEWEQKITALLEQAQIQQ EKNEYELQKLDKWASLWEWF-Z (SEQ ID NO:1).

7. The method of claim 6 wherein X is an acetyl group.

8. The method of claim 6 wherein Z is an amido group.

9. The method of claim 6 wherein X is an acetyl group and Z is an amido group.

10. The method of claim 6 wherein X is a protecting group, and wherein the method further comprises the step of modifying X into an acetyl group.

11. The method of claim 10 wherein Z is an amido group.

12. The method of claim 1 wherein X is an acetyl group.

13. The method of claim 1 wherein Z is an amido group.

14. The method of claim 1 wherein X is an acetyl group and Z is an amido group.

15. The method of claim 1 wherein X is a protecting group, and wherein the method further comprises the step of modifying X into an acetyl group.

16. The method of claim 15 wherein Z is an amido group.

17. The method of claim 1 wherein the side-chain protected peptide of the formula X-WQEWEQKITALL-COOH (SEQ ID NO:2) is synthesized by solid phase peptide synthesis.

18. The method of claim 1 wherein the side-chain protected peptide of the formula EQAQIQQEKNEYELQKLDKWASLWEWF-Z (SEQ ID NO:6) is synthesized by a method comprising reacting a side-chain protected peptide of the formula QKLDKWASLWEWF-Z (SEQ ID NO:5) to yield the side-chain protected peptide of the formula EQAQIQQEKNEYELQKLDKWASLWEWF-Z (SEQ ID NO:6), wherein the amino terminus of a QKLDKWASLWEWF-Z (SEQ ID NO:5) is deprotected with a side-chain protected peptide of the formula EQAQIQQEKNEYEL-COOH (SEQ ID NO:3).

19. The method of claim 18 wherein the side-chain protected peptide of the formula QXLDKWASLWEWF-Z (SEQ ID NO:5) is synthesized by a method comprising reacting a side-chain protected peptide of the formula QKLDKWASLWEW-COOH (SEQ ID NO:4) with phenylalanine amide to yield the side-chain protected peptide of the formula QKLDKWASLWEWF-Z (SEQ ID NO:5).

20. The method of claim 19, wherein the side-chain protected peptide of the formula QKLDKWASLWEW-COOH (SEQ ID NO:4) is synthesized by solid phase peptide synthesis.

21. The method of claim 18, wherein the side-chain protected peptide of the formula EQAQIQQEKNEYEL-COOH (SEQ ID NO:3) is synthesized by solid phase peptide synthesis.

22. A method for synthesizing a peptide of the formula EQAQIQQEKNEYELQKLDKWASLWEWF-Z (SEQ ID NO:6) comprising reacting a side-chain protected peptide of the formula QKLDKWASLWEWF-Z (SEQ ID NO: 5) to yield the side-chain protected peptide of the formula EQAQIQQEKNEYELQKLDKWASLWEWF-Z (SEQ ID NO: 6), wherein the amino terminus of QKLDKWASLWEWF-Z (SEQ ID NO: 5) is deprotected with a side-chain protected peptide of the formula EQAQIQQEKNEYEL-COOH (SEQ ID NO: 3).

23. The method of claim 22 wherein the side-chain protected peptide of the formula QKLDKWASLWEWF-Z (SEQ ID NO:5) is synthesized by a method comprising reacting a side-chain protected peptide of the formula QKLDKWASLWEW-COOH (SEQ ID NO:4) with phenylalanine amide to yield the side-chain protected peptide of the formula QKLDKWASLWEWF-Z (SEQ ID NO:5).

24. The method of claim 23, wherein the side-chain protected peptide of the formula QKLDKWASLWEW-COOH (SEQ ID NO:4) is synthesized by solid phase peptide synthesis.

25. The method of claim 22, wherein the side-chain protected peptide of the formula EQAQIQQEKNEYEL-COOH (SEQ ID NO:3) is synthesized by solid phase peptide synthesis.

* * * * *

SEQUENCE LISTING

<160> NUMBER OF SEQ ID NOS: 8

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 1

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
                20                  25                  30

Ala Ser Leu Trp Glu Trp Phe
         35

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 2

Trp Gln Glu Trp Glu Gln Lys Ile Thr Ala Leu Leu
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 3

Glu Gln Ala Gln Ile Gln Gln Glu Lys Asn Glu Tyr Glu Leu
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 4

Gln Lys Leu Asp Lys Trp Ala Ser Leu Trp Glu Trp
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 5

Gln Lys Leu Asp Lys Trp Ala Ser Leu Trp Glu Trp Phe
 1               5                  10

```
<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 6

Glu Gln Ala Gln Ile Gln Gln Glu Lys Asn Glu Tyr Glu Leu Gln Lys
 1               5                  10                  15

Leu Asp Lys Trp Ala Ser Leu Trp Glu Trp Phe
            20                  25

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 7

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu
            20                  25

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Peptide
      Fragments

<400> SEQUENCE: 8

Glu Gln Ala Gln Ile Gln Gln Glu Lys Asn Glu Tyr Glu Leu Gln Lys
 1               5                  10                  15

Leu Asp Lys Trp Ala Ser Leu Trp Glu Trp
            20                  25
```